United States Patent
Homann et al.

(10) Patent No.: US 6,410,306 B1
(45) Date of Patent: Jun. 25, 2002

(54) ENANTIOSELECTIVE ENZYMATIC HYDROLYSIS OF 3-SUBSTITUTED ESTERS OF GLUTARIC ACID

(75) Inventors: Michael J. Homann, Clinton; William B. Morgan, Chatham Township; Aleksey Zaks, Hoboken, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/512,247

(22) Filed: Feb. 24, 2000

Related U.S. Application Data

(60) Provisional application No. 60/121,749, filed on Feb. 26, 1999.

(51) Int. Cl.[7] .............................. C12P 7/40; C12P 7/22
(52) U.S. Cl. ..................... 435/280; 435/135; 435/136; 435/156; 435/142
(58) Field of Search .................. 435/280, 156, 435/142, 36, 135

(56) References Cited

U.S. PATENT DOCUMENTS 5,198,568 A    3/1993  Zepp et al. .................... 560/60

OTHER PUBLICATIONS

Chen, et al., "Asymmetric Synthesis of Substituted 2–Azaspiro[3.5]nonan–1–ones: An Enantioselective Synthesis of the Cholesterol Absorption Inhibitor (+)–SCH 54016, " *J. Org. Chem.*, vol. 61, pp. 8341–8343 (1996).

Chênevert, et al., "Chemoenzymatic Enantioselective Synthesis of Baclofen," *Can. J. Chem.*, vol. 72, pp. 2312–2317 (1994).

Chênevert, et al., "Chemoenzymatic Synthesis of Both Enantiomers of Baclofen," *Tetrahedron Letters*, vol. 32, No. 34, pp. 4249–4250 (1991).

*Primary Examiner*—Irene Marx
(74) *Attorney, Agent, or Firm*—William Y. Lee; Arthur Mann

(57) ABSTRACT

A process is provided for preparing an S-enantiomer compound having the formula

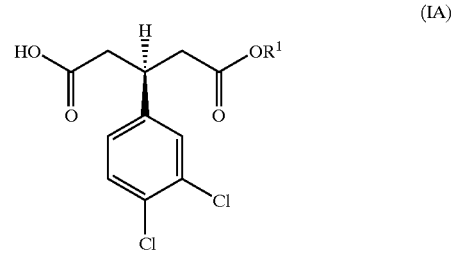

in enantiomeric excess, or an R-enantiomer compound having the formula

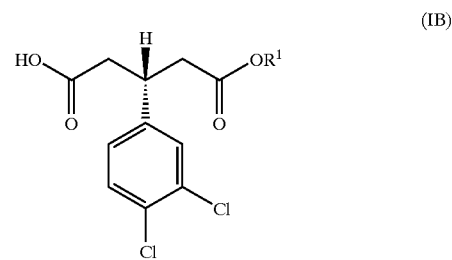

in enantiomeric excess, said process comprising hydrolyzing a compound having the formula

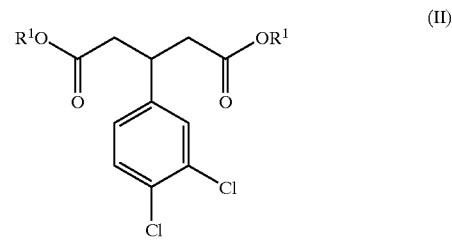

with:

(a) an enzyme capable of producing an enantiomeric excess of the S-enantiomer compound of formula (IA) of at least 70%, or (b) an enzyme capable of producing an enantiomeric excess of the R-enantiomer compound of formula (IB) of at least 70%, wherein $R^1$ is selected from the group consisting of alkyl, aryl, aralkyl, cycloalkyl, or cycloalkylalkyl.

19 Claims, No Drawings

ENANTIOSELECTIVE ENZYMATIC HYDROLYSIS OF 3-SUBSTITUTED ESTERS OF GLUTARIC ACID

This application claims the benefit of U.S. Provisional Application No. 60/121,749, filed Feb. 26, 1999.

BACKGROUND OF THE INVENTION

Substituted oximes are useful pharmaceutical compounds. For example, International Application No. PCT/US98/23255, filed Nov. 18, 1998, describes certain substituted oximes that are useful as neurokinin antagonists. In many instances, it is desireable to produce a particular enantiomer of the substituted oxime. Thus, any efficient enantioselective process for producing a chiral intermediate for these compounds would be a welcome contribution to the art. This invention provides such a contribution.

SUMMARY OF THE INVENTION

This invention provides a process for preparing an S-enantiomer compound having the formula

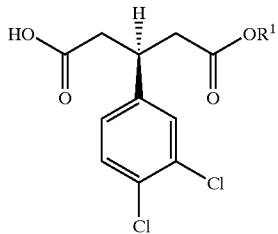

(IA)

in enantiomeric excess, or an R-enantiomer compound having the formula

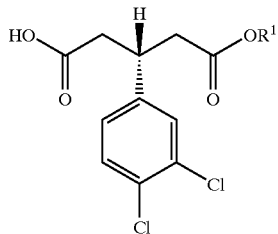

(IB)

in enantiomeric excess, said process comprising hydrolyzing a compound having the formula

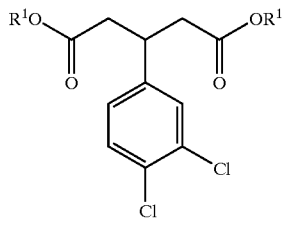

(II)

with:
(a) an enzyme capable of producing an enantiomeric excess of the S-enantiomer compound of formula (IA) of at least 70%, or
(b) an enzyme capable of producing an enantiomeric excess of the R-enantiomer compound of formula (IB) of at least 70%, wherein $R^1$ is selected from the group consisting of alkyl, aryl, aralkyl, cycloalkyl, or cycloalkylalkyl.

DETAILED DESCRIPTION OF THE INVENTION

As used herein, the term "alkyl" means straight or branched hydrocarbon chains of 1 to 6 carbon atoms, optionally substituted with one or more halo, hydroxy, or alkoxy substituents.

"Alkoxy" refers to a group having the formula R—O—, wherein R is alkyl.

"Aryl" refers to a carbocyclic group having at least one aromatic ring (e.g., phenyl or naphthyl), optionally substituted with one or more substituents selected from halo, alkyl, hydroxy, alkoxy, or —CF3.

"Aralkyl" refers to a group having the formula aryl-R—, wherein R is alkyl.

"Cycloalkyl" refers to a non-aromatic carbocyclic ring of from 3 to 6 carbon atoms, optionally substituted with one or more substituents selected from halo, alkyl, hydroxy, alkoxy, or —CF3.

"Cycloalkylalkyl" refers to a group having the formula cycloalkyl-R—, wherein R is alkyl.

"Halo" refers to fluorine, chlorine, bromine or iodine.

"Et" refers to an ethyl group.

"Enantiomeric excess" is calculated according to the following formula:

$$\text{e.e. } \% = \frac{|[R] - [S]|}{[R] + [S]} \times 100\%$$

where [R] is the concentration of the R-enantiomer, and [S] is the concentration of the S-enantiomer.

$R^1$ is preferably alkyl, more preferably methyl or ethyl, most preferably ethyl.

Enzymes suitable for use in the present process can be identified by carrying out the screening procedure described in Example 1, below. The enzyme is preferably one that is capable of producing an e.e. of the desired compound of at least 80%, more preferably at least 90%. Preferably, the enzyme is one that produces the S-enantiomer compound in enantiomeric excess.

Preferably, the enzymes used for preparing the S-enantiomer compound of formula (IA) are produced by *Candida rugosa, Candida cylindracea, Candida antarctica,* and *Rhizopus delemar*. Examples of enzymes suitable for use in preparing the S-enantiomer compound of formula (IA) include, but are not limited to, the following commercially available enzyme preparations: Altus ChiroCLEC CRO (*Candida rugosa*); Altus ChiroCLEC-CR (*Candida rugosa*); Altus Lipase CR Analytical Grade 001-C (*Candida rugosa*); Biocatalysts Ltd. (*Candida cylindracea*); Meito Sangyo LIPASE-OF (*Candida cylindracea*); Boehringer Mannheim Cholesterol Esterase (*Candida rugosa*); Boehringer Mannheim CHIRAZYME L-2 (*Candida antarctica*, fraction B); Fluka Lipase (*Candida antarctica*); Genzyme Lipase (*Candida cyclindracea*); Novo Nordisk Novozym 435 (*Candida antarctica*, type B); Novo Nordisk SP 525 (*Candida antarctica*, type B); and Seikagaki Lipase (*Rhizopus delemar*). Of these commercially available enzyme preparations, Boehringer Mannheim CHIRAZYME L-2, in either the dry or liquid form, and Novo Nordisk Novozym 435 (*Candida antarctica*, type B), in either the dry or liquid form, are particularly preferred.

Preferably, the enzymes used for preparing the R-enantiomer compound of formula (IB) are obtained from porcine or bovine pancreas. Examples of enzymes suitable for use in preparing the R-enantiomer compound of formula (IB) include, but are not limited to, the following commercially available enzyme preparations: Biocatalysts Ltd. Lipase (porcine pancreas); Boehringer Mannheim Lipase (porcine pancreas); Boehringer Mannheim CHIRAZYME L-7 Lipase (porcine pancreas); Rohm Tech COROLASE PP (porcine pancreas); Scientific Protein Labs. PEC High Lipase; Sigma α-Chymotrypsin Type II (bovine pancreas); Sigma Trypsin (porcine pancreas); Sigma Lipase Type II (porcine pancreas); ThermoGen ThermoCat E001; ThermoGen ThermoCat E002; ThermoGen ThermoCat E003; ThermoGen ThermoCat E004; ThermoGen ThermoCat E005; ThermoGen ThermoCat E006; ThermoGen ThermoCat E007; ThermoGen ThermoCat E008; ThermoGen ThermoCat E009; ThermoGen ThermoCat E010; ThermoGen ThermoCat E011; ThermoGen ThermoCat E012; ThermoGen ThermoCat E013; ThermoGen ThermoCat ThermoCat E014; ThermoGen ThermoCat E015; ThermoGen ThermoCat E016; ThermoGen ThermoCat E017B; ThermoGen ThermoCat 018; ThermoGen ThermoCat 019; ThermoGen ThermoCat 020; and ThermoGen ThermoCat 027. Of these commercially available enzyme preparations, Sigma α-Chymotrypsin Type II and Boehringer Mannheim CHIRAZYME L-7 are particularly preferred.

The hydrolysis of compound (II) is preferably carried out at a pH of 5–9, more preferably 6–8.5, most preferably 7–8. Preferably, the substrate concentration is 5% to 25%, more preferably 8% to 12%. Preferably, the hydrolysis is carried out at a temperature of 25° to 45° C., more preferably, 30° to 40° C. The hydrolysis is preferably carried out in the presence of a buffer (e.g., sodium phosphate or potassium phosphate buffer), and the reaction may, if desired, be titrated with a caustic titrant (e.g., NaOH solution) to maintain the pH within the preferred range. Preferably, the concentration of the caustic titrant is 0.2 to 1 M, preferably about 0.5 M. In a particularly preferred embodiment, compound (II) is dispersed in a buffer solution by agitation, and the enzyme is subsequently added to the mixture. Upon adding the enzyme, the reaction mixture is agitated until the desired degree of hydrolysis is reached. When using an enzyme in solid form (e.g., adsorbed on beads), the reaction may be terminated by removing the enzyme by filtration, and adding acid (e.g., $H_2SO_4$) to the filtrate to adjust the pH to about 4.0–4.5, thereby precipitating the desired product. When using a liquid enzyme, the reaction may be terminated by adding acid (e.g., $H_2SO_4$) to adjust the pH to about 4.0–4.5, and the precipitated product can be recovered by filtration.

Compound (II) may be made by conventional means, e.g., as shown in the scheme below:

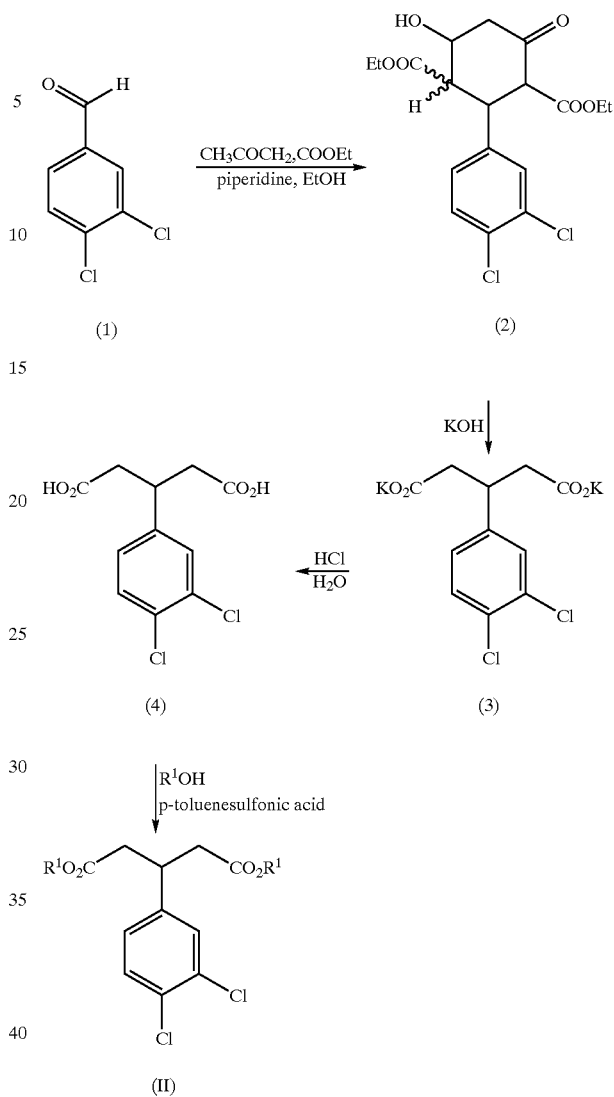

As shown in the scheme above, aldehyde (1) is condensed with ethyl acetoacetate in ethyl alcohol with a piperidine catalyst to form crude reaction product (2), a mixture of 2 isomers. The condensation is preferably carried out over 2–3 days at 20° C.±5° C. Potassium hydroxide is added to the crude reaction product (2), and heated at about 60°–70° C. for about one hour to form dipotassium salt (3), which is filtered and washed with ethyl alcohol. The dipotassium salt is dissolved in water and treated with HCl to form compound (4). Compound (4) is reacted with an alcohol, $R^1OH$ (e.g., ethyl alcohol) in the presence of p-toluenesulfonic acid to form compound (II). Compound (II) may be isolated and purified by adding a higher boiling solvent, (e.g., heptane), distilling off the alcohol, washing with dilute sodium bicarbonate solution to remove the p-toluenesulfonic acid, and cooling the solution to precipitate compound (II).

The following examples illustrate the foregoing invention, although such examples should not be construed as limiting the scope of the invention. Alternative reagents and analagous processes within the scope of the invention will be apparent to those skilled in the art.

EXAMPLES

Example 1

Enzyme screening reactions were conducted using 1–30 mg enzyme suspended in 0.9 ml of 50 mM sodium phosphate buffer pH 7. The reaction was initiated upon addition of ethyl 3-[3',4'-dichlorophenyl]glutarate (~25 mg) dissolved in 0.1 ml acetone (10% v/v). Following 48 hours of incubation in 1 dram vials at 30° C. with agitation (225 rpm), the reactions were terminated by acidification to a pH of less than 2 using 6N HCl and extracted with 2 ml ethyl acetate prior to analysis by reverse-phase and chiral HPLC. Enzymes generating the R-monoester or the S-monoester in ≧87% enantiomeric excess are summarized in Tables 1 and 2, respectively.

TABLE 1

Enzymes identified to selectively hydrolyze precursor ethyl 3-[3',4'-dichlorophenyl]glutarate yielding R - monoacid.

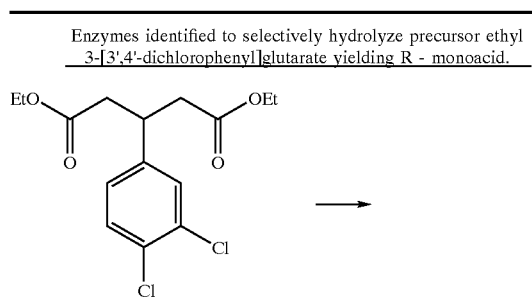

| Vendor | Enzyme (mg used) | EE, % | Configuration ("S"/"R") | % Yield |
| --- | --- | --- | --- | --- |
| Biocatalysts | Lipase Porcine Pancreatic (26.2) | 100 | R | 12 |
| Sigma | Lipase Type II: Porcine Pancreas (30) | 100 | R | 5 |
| Solvay | Lipase pancreatic, 250 (30) | 100 | R | 7 |
| Sci. Prot. Lab | PEC High Lipase (27.8) | 100 | R | 17 |
| Sigma | Chymotrypsin type II: Bovine pancreas (27.7) | 100 | R | 26 |
| Sigma | Trypsin: procine pancreas (29.9) | 97 | R | 16 |
| Rohm | Corolase PP: Porcine pancreas (30) | 100 | R | 5 |
| Boehringer Mannheim | chirazyme L7 (30) | 100 | R | 20 |
| ThermoGen | ThermoCat E001 (1 mg) | 95 | R | 27 |
| ThermoGen | ThermoCat E002 (1 mg) | 90 | R | 10 |
| ThermoGen | ThermoCat E003 (1 mg) | 97 | R | 39 |
| ThermoGen | ThermoCat E004 (1 mg) | 95 | R | 22 |
| ThermoGen | ThermoCat E005 (1 mg) | 96 | R | 30 |
| ThermoGen | ThermoCat E006 (1 mg) | 96 | R | 37 |
| ThermoGen | ThermoCat E008 (1 mg) | 95 | R | 38 |
| ThermoGen | ThermoCat E010 (1 mg) | 95 | R | 30 |
| ThermoGen | ThermoCat E011 (1 mg) | 95 | R | 31 |
| ThermoGen | ThermoCat E012 (1 mg) | 96 | R | 32 |
| ThermoGen | ThermoCat E013 (1 mg) | 93 | R | 22 |
| ThermoGen | ThermoCat E014 (1 mg) | 94 | R | 35 |

TABLE 1-continued

Enzymes identified to selectively hydrolyze precursor ethyl 3-[3',4'-dichlorophenyl]glutarate yielding R - monoacid.

| Vendor | Enzyme (mg used) | EE, % | Configuration ("S"/"R") | % Yield |
| --- | --- | --- | --- | --- |
| ThermoGen | ThermoCat E015 (1 mg) | 94 | R | 26 |
| ThermoGen | ThermoCat E0017B (1 mg) | 94 | R | 35 |
| ThermoGen | ThermoCat E019 (1 mg) | 96 | R | 27 |
| ThermoGen | ThermoCat E020 (1 mg) | 96 | R | 40 |
| Thermogen | ThermoCat E027 (25 mg) | 97 | R | 66 |

TABLE 2

Enzymes identified to selectively hydrolyze precursor ethyl 3-[3',4'-dichlorophenyl]glutarate yielding S - monoacid.

| Vendor | Enzyme (mg used) | EE, % | Configuration ("S"/"R") | % Yield |
| --- | --- | --- | --- | --- |
| Biocatalysts | Lipase *Candida cylindracea* (28.8) | 87 | S | 14 |
| Genzyme | Lipase *Candida cylindracea* (26.7) | 100 | S | 32 |
| Meito Sangyo | Lipase OF: *C. cylindracea* (28.3) | 89 | S | 13 |
| Novo | Novozyme 435: *Candida antarctica*, type B (27.7) | 100 | S | 59 |
| Novo | SP 525 Lipase: *Candida antarctica*, type B (28.8) | 100 | S | 31 |

TABLE 2-continued

Enzymes identified to selectively hydrolyze precursor ethyl
3-[3',4'-dichlorophenyl]glutarate yielding S - monoacid.

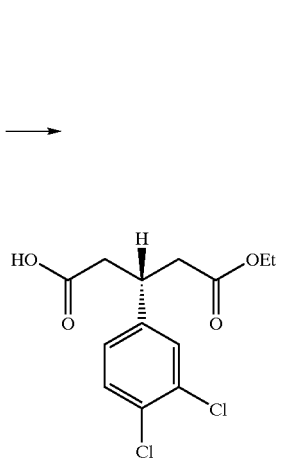

| Vendor | Enzyme (mg used) | EE, % | Config- uration ("S"/"R") | % Yield |
|---|---|---|---|---|
| Seikagaki | Lipase: *Rhizopus delemar* (26.9) | 100 | S | 40 |
| Boehringer Mannheim | Cholesterol esterase: *Candida cylindracea* (27.3) | 100 | S | 65 |
| Fluka | Lipase: *Candida antarctica* (25.8) | 95 | S | 19 |
| Boehringer Mannheim | chirazyme L2 (28.3) | 100 | S | 31 |
| Altus | ChiroCLEC CRO: *C. rugosa* from Meito Sangyo OF (10) | 100 | S | 10 |
| Altus | ChiroCLEC-CR (50) | 100 | S | 19 |
| Altus | Lipase CR: A. Grade 001- *C. rugosa* from Meito Sangyo OF (25.5) | 100 | S | 30 |

Example 2
Multigram Scale Preparation of R-monoethyl Ester

Ethyl 3-(3',4'-dichlorophenyl)glutarate (2.45 g, 7.35 mmol) was added to 50 mM KCl (400 mL) in a 3-neck round bottom flask equipped with an electrode and pH delivery tube connected to a pH stat. The mixture was stirred and adjusted to pH 7–8. α-chymotrypsin (Sigma Type II; bovine pancreas) (1.25 g) was added and the pH was maintained at pH 8 by automatic titration of 0.5 M NaOH. The reaction was terminated after 114 hours. The reaction mixture was evaporated to dryness and the resultant solid triturated with methylene chloride (200 mL). The slurry was filtered and the filtrate evaporated to dryness to obtain a pink oil which slowly solidified: 2.12 g, 94.6% yield; >95% enantiomeric excess; [ ]$^{25}_D$=−5.77 (c=1.11, EtOH).

Example 3
Multigram Scale Preparation of S-monoethyl Ester Using Chirazyme L-2 (Adsorbed on Beads)

Ethyl 3-[3',4'-dichlorophenyl]glutarate (135 g) was dispersed in 10 mM sodium phosphate buffer pH 8.0 (1215 ml) using an impeller mixer mounted in a 3-neck round bottom jacketed glass flask (3 L) equipped with an electrode and pH delivery tube connected to a pH stat. The mixture was stirred and adjusted to pH 8 at 40° C. The reaction was initiated with the addition of 33.75 g of Chirazyme L-2 (adsorbed on beads) and pH 8.0 was maintained by automatic titration of 0.5 M sodium hydroxide. Following 24 hours of incubation, the reaction was 96% monoester as measured by HPLC. The reaction was terminated by removing the enzyme by filtration. The pH of the filtrate was adjusted to 4.0–4.5 using 20% $H_2SO_4$ followed by isolation of the precipitated product by filtration. The acid precipitant was dried (vacuum dryer), and then dissolved in 300 ml of tert-butyl methyl ether (TBME). Insoluble material was removed by filtration through celite. The TBME filtrate was mixed with 400–600 ml of n-heptane and vacuum evaporated to remove the TBME. Removal of TBME resulted in precipitation of the desired S-monoester. Residual ethyl 3-[3',4'-dichlorophenyl] glutarate diester remains dissolved in n-heptane. The precipitated slurry was filtered and the filtercake dried in a vacuum oven yielding a fluffy white powder; 104.07 g, 84% molar yield; >99% enantiomeric excess. Molar yields of 98% S-monoester in >99% enantiomeric excess were obtained using similar conversion conditions employing 5 g of Chirazyme L-2 (covalently bound to beads) and 20 g of ethyl 3-[3',4'-dichlorophenyl]glutarate.

Example 4
Multigram Scale Preparation of S-monoethyl Ester Using Chirazyme L-2 (Liquid)

Ethyl 3-[3',4'-dichlorophenyl]glutarate (20 g) was dispersed in 25 mM sodium phosphate buffer pH 7.5 (180 ml) using an impeller mixer mounted in a 3-neck round bottom jacketed glass flask (500 mL) equipped with an electrode and pH delivery tube connected to a pH stat. The mixture was stirred and adjusted to pH 7.5 at 30–38° C. The reaction was initiated with the addition of 10 ml of Chirazyme L-2 (liquid form) and pH 7.5 was maintained by automatic titration of 0.5 M sodium hydroxide. Molar yields of >95% S-monoester in >99% enantiomeric excess were achieved following 24–32 hours of incubation based on volume of titrant added and chiral HPLC analysis. The reaction was terminated by adjusting the pH to 4.0–4.5, followed by isolation of the precipitated product as outlined in Example 3.

Example 5
Pilot Scale kg Preparation of S-monoethyl Ester Using Chirazyme L-2 (Adsorbed on Beads)

Ethyl 3-[3',4'-dichlorophenyl]glutarate (50 kg) was dispersed in 10 mM sodium phosphate buffer pH ~8.0 ( 450 L) with agitation (impeller speed ~100 rpm) at 40° C. in a 300 gallon glass-lined reactor equipped with an in-vessel pH probe. The reaction was initiated with the addition of 6.25 kg of Chirazyme L-2 (adsorbed on beads). Control of reaction pH between 7.9–8.1 was achieved manually by observing the in-vessel probe and manually adjusting a metering valve to regulate flow of caustic (0.5 M NaOH) from an adjacent feedbottle pressurized with 3 psi nitrogen. A 93% conversion yield was achieved at 38–40° C. following 43 hours of incubation. The reaction was terminated by removing the enzyme by filtration. The enzyme filtercake was washed with 100 mM phosphate buffer pH ~8.0 (~125 L). The filtercake wash and filtrate were combined in a 200 gallon reactor and the pH was adjusted to ~4.2 using 10% $H_2SO_4$ followed by isolation of the precipitated product by filtration. The acid precipitant was rinsed in situ with water (~100 L) and dried on trays in an air dryer, yielding 40.5 kg product in >99 % enantiomeric excess. Dried cake from two batch reactions (~79 kg) was mixed with 6 kg of supercel and 320 L tert-butyl methyl ether (TBME). Insoluble material and supercel were removed by filtration and rinsed with 110 L of TBME. The rinse was combined with the filtrate and concentrated 2–3 fold by vacuum evaporation. The TBME concentrate was mixed with ~640 L of n-heptane and vacuum evaporated to remove the TBME. Removal of TBME resulted in precipitation of the desired S-monoester. Residual ethyl 3-[3',4'-dichlorophenyl]glutarate remains dissolved in n-heptane. The precipitated slurry was filtered and the filtercake was dried in a vacuum oven, yielding a white powder; 75.2 kg, 82.1% molar yield; >99% enantiomeric excess; [ ]$^{20}_D$=+6.9 (c=1.0075, EtOH).

Example 6

Pilot Scale kg Preparation of S-monoethyl Ester Using Chirazyme L-2 (Liquid)

Ethyl 3-[3',4'-dichlorophenyl]glutarate (6.5 kg) was dispersed in 25 mM sodium phosphate buffer pH ~8.0 (~60 L) with agitation (impeller speed ~100 rpm) at 30° C. in a 50 gallon glass-lined reactor equiped with an in-vessel pH probe. The reaction was initiated with the addition of 3.25 L of Chirazyme L-2 (liquid). Control of reaction pH between 7.9–8.1 was achieved manually by observing the in-vessel probe and manually adjusting a metering valve to regulate flow of caustic (0.5 M NaOH) from an adjacent portable can pressurized with nitrogen (20 psi). A 97% molar yield was achieved at 30° C. following 45 hours of incubation. The reaction was terminated by reducing the pH to ~4.2 using 10% $H_2SO_4$ followed by isolation of the precipitated product by filtration. The acid precipitant was rinsed in situ with water (~13 L) and dried on trays in an air dryer, yielding 5.8 kg product in >99 % enantiomeric excess. Dried cake from two batch reactions (~11.4 kg) was mixed with 2 kg of supercel and 50 L tert-butyl methyl ether (TBME). Insoluble material and supercel were removed by filtration and rinsed with 11 L of TBME. The rinse was combined with the filtrate and concentrated 2–3 fold by vacuum evaporation. The TBME concentrate was mixed with ~110 L of n-heptane and vacuum evaporated to remove the TBME. Removal of TBME resulted in precipitation of the desired S-monoester. Residual ethyl 3-[3',4'-dichlorophenyl]glutarate remains dissolved in n-heptane. The precipitated slurry was filtered and the filtercake dried in a vacuum oven yielding a white powder; 9.7 kg, 81.4% molar yield; >99% enantiomeric excess.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A process for preparing an S-enantiomer compound having the formula

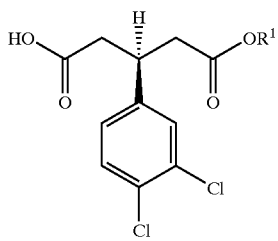

(IA)

in enantiomeric excess, or an R-enantiomer compound having the formula

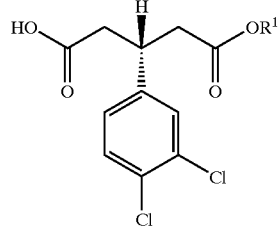

(IB)

in enantiomeric excess, said process comprising hydrolyzing a compound having the formula

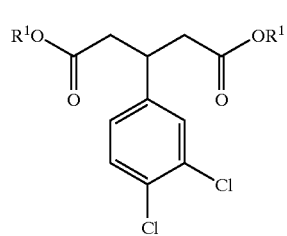

(II)

with:
(a) an enzyme capable of producing an enantiomeric excess of the S-enantiomer compound of formula (IA) of at least 70%, or
(b) an enzyme capable of producing an enantiomeric excess of the R-enantiomer compound of formula (IB) of at least 70%, wherein $R^1$ is independently selected from the group consisting of alkyl, aryl, aralkyl, cycloalkyl and cycloalkylalkyl,
and recovering said S-enantiomer or R-enantiomer from said process.

2. The method of claim 1, wherein the enzyme used is one that produces an enantiomeric excess of the S-enantiomer of at least 70%.

3. The method of claim 2, wherein an enantiomeric excess of the S-enantiomer of at least 80% is produced.

4. The method of claim 3, wherein the hydrolysis is carried out at a temperature of from 25° to 45° C.

5. The method of claim 4, wherein an enantiomeric excess of the S-enantiomer of at least 90% is produced.

6. The method of claim 5, wherein the hydrolysis is carried out at a temperature of from 30° to 40° C.

7. The method of claim 6, wherein the hydrolysis is carried out in the presence of a buffer.

8. The method of claim 7, wherein the hydrolysis is carried out at a pH from 6–8.5.

9. The method of claim 8, wherein the enzyme is produced by an organism selected from the group consisting of *Candida rugosa, Candida cylindracea, Candida antarctica,* and *Rhizopus delemar.*

10. The method of claim 9, wherein the hydrolysis is carried out at a pH from 7–8.

11. The method of claim 1, wherein the enzyme used is one that produces an enantiomeric excess of the R-enantiomer of at least 70%.

12. The method of claim 11, wherein an enantiomeric excess of the R-enantiomer of at least 80% is produced.

13. The method of claim 12, wherein the hydrolysis is carried out at a temperature of from 25° to 45° C.

14. The method of claim 13, wherein an enantiomeric excess of the R-enantiomer of at least 90% is produced.

15. The method of claim 14, wherein the hydrolysis is carried out at a temperature of from 30° to 40° C.

16. The method of claim 15, wherein the hydrolysis is carried out in the presence of a buffer.

17. The method of claim 16, wherein the hydrolysis is carried out at a pH from 6–8.5.

18. The method of claim 17, wherein the enzyme is obtained from porcine or bovine pancreas.

19. The method of claim 18, wherein the hydrolysis is carried out at a pH from 7–8.

* * * * *